United States Patent
Rogachefsky et al.

(10) Patent No.: US 10,004,916 B2
(45) Date of Patent: Jun. 26, 2018

(54) ORTHOPEDIC FIXATION DEVICE WITH MAGNETIC FIELD GENERATOR

(71) Applicant: Richard A. Rogachefsky, San Pedro, CA (US)

(72) Inventors: Richard A. Rogachefsky, San Pedro, CA (US); James Seal, Boca Raton, FL (US)

(73) Assignee: Richard A. Rogachefsky, San Pedro, CA (US)

( * ) Notice: Subject to any disclaimer, the term of this patent is extended or adjusted under 35 U.S.C. 154(b) by 734 days.

(21) Appl. No.: 14/547,513

(22) Filed: Nov. 19, 2014

(65) Prior Publication Data

US 2015/0080636 A1    Mar. 19, 2015

Related U.S. Application Data

(63) Continuation of application No. 13/337,584, filed on Dec. 27, 2011, now abandoned.

(51) Int. Cl.
| | |
|---|---|
| *A61N 2/02* | (2006.01) |
| *A61B 17/80* | (2006.01) |
| *A61B 17/72* | (2006.01) |
| *A61N 2/00* | (2006.01) |
| *A61B 17/86* | (2006.01) |

(52) U.S. Cl.
CPC ............ *A61N 2/02* (2013.01); *A61B 17/72* (2013.01); *A61B 17/80* (2013.01); *A61B 17/86* (2013.01); *A61N 2/002* (2013.01); *A61N 2/008* (2013.01)

(58) Field of Classification Search
CPC .......... A61B 17/72–17/7291; A61N 2/00–2/12
USPC .............. 600/9–15; 606/53–86 B, 280–299; 607/51–52
See application file for complete search history.

(56) References Cited

U.S. PATENT DOCUMENTS

| | | | |
|---|---|---|---|
| 3,745,995 A | * 7/1973 | Kraus | A61B 17/58 602/2 |
| 3,820,534 A | 6/1974 | Kraus | |
| 5,411,503 A | * 5/1995 | Hollstien | A61B 17/1707 606/80 |
| 6,778,861 B1 | 8/2004 | Liebrecht et al. | |
| 2004/0138663 A1 | 7/2004 | Kosashvili et al. | |

(Continued)

FOREIGN PATENT DOCUMENTS

| | | |
|---|---|---|
| GB | 1466337 A | 3/1977 |
| JP | 2007283110 A | 11/2007 |
| WO | 2011051947 A1 | 5/2011 |

OTHER PUBLICATIONS

PCT Notification of Transmittal of the International Search Report and the Written Opinion of the International Searching Authority, or the Declaration, dated Apr. 5, 2013 (2 pages).

(Continued)

*Primary Examiner* — Catherine B Kuhlman
(74) *Attorney, Agent, or Firm* — Knobbe, Martens, Olson & Bear LLP (57) ABSTRACT

A medical device includes an orthopedic fixation device and an electromagnetic field emitter carried by the fixation device. The device preferably further includes a power source for powering the electromagnetic field emitter, which may be implanted in the human body with the fixation device and the electromagnetic field emitter. The power source may be a battery.

25 Claims, 7 Drawing Sheets

(56) References Cited

U.S. PATENT DOCUMENTS

| | | | |
|---|---|---|---|
| 2005/0070916 A1* | 3/2005 | Hollstien | A61B 17/1725 606/96 |
| 2005/0075562 A1 | 4/2005 | Szakelyhidi, Jr. et al. | |
| 2006/0079897 A1 | 4/2006 | Harrison et al. | |
| 2007/0265628 A1* | 11/2007 | Kraus | A61B 17/72 606/64 |
| 2008/0255556 A1 | 10/2008 | Berger | |
| 2009/0099404 A1* | 4/2009 | Kraus | A61B 17/86 600/13 |
| 2010/0131024 A1 | 5/2010 | Lathrop et al. | |
| 2010/0145337 A1* | 6/2010 | Janna | A61B 17/1707 606/67 |

OTHER PUBLICATIONS

PCT International Search Report, dated Apr. 5, 2013 (4 pages).
PCT Written Opinion of the International Searching Authority, or the Declaration, dated Apr. 5, 2013 (6 pages).
EPO Communication dated Oct. 7, 2015 (7 pages).
JPO Communication dated Nov. 29, 2016 (Sumarized English Translation, 3 pages).

* cited by examiner

ORTHOPEDIC FIXATION DEVICE WITH MAGNETIC FIELD GENERATOR

CROSS-REFERENCE TO RELATED APPLICATIONS

This application is a continuation of and claims priority to, copending application U.S. Ser. No. 13/337,584, filed Dec. 27, 2011, the disclosure of which is incorporated by reference herein in its entirety.

FIELD OF THE INVENTION

This disclosure relates to orthopedics. More specifically, the invention relates to an orthopedic fixation device with an integrated magnetic field generator for placement in a patient to promote healing of a fractured bone and surrounding tissue, to reduce infection, reduce both acute and chronic pain, in arthrodesis procedures, and to reduce edema, as well as for other purposes.

RELATED ART

Electromagnetic fields have been proposed for use for therapeutic purposes for many years. Heretofore, fields have been generated externally and oriented so as to pass through the tissue or bone to be treated. The systems, while effective, have the disadvantage that they require bulky signal generating apparatus and electromagnetic field generating coils to be worn by the patient. This is a particular problem for patients who are ambulatory and a lesser but still significant problem for patients confined to bed.

SUMMARY OF THE INVENTION

The present disclosure remedies the foregoing shortcomings of the prior art by providing an improved medical device for implanting in a patient.

In one aspect of the invention, a device includes an orthopedic fixation device and an electromagnetic field emitter carried by the fixation device. The orthopedic fixation device may be a rod or plate or similar device. The device preferably further includes a power source for powering the electromagnetic field emitter, and a controller that may be separate from or integrated with the power source for generating a varying signal that is applied to the electromagnetic field emitter, all of which may be implanted in the human body with the fixation device and the electromagnetic field emitter. The power source may be a battery.

In another aspect of the invention, a device for use in healing a broken bone includes an internal fixation device having an opening or cavity therein and an electromagnetic field emitter disposed in the opening or cavity.

In accordance with another aspect of the invention a device for use in healing a broken bone and for other uses includes an internal fixation device carrying an electromagnetic field generator, a signal generator, and a rechargeable power source, together with an external device for recharging the power source.

An understanding of these and other aspects, features, and benefits of the invention may be had with reference to the attached figures and following disclosure, in which preferred embodiments of the invention are illustrated and described.

DETAILED DESCRIPTION OF PREFERRED EMBODIMENTS OF THE INVENTION

The invention relates generally to fixation devices. More specifically, the invention relates to fixation devices that are useful for assisting in fracture and wound healing, treating infection, reducing pain, and for other therapeutic purposes. Preferred embodiments of the invention now will be described with reference to the figures.

Figure 1:
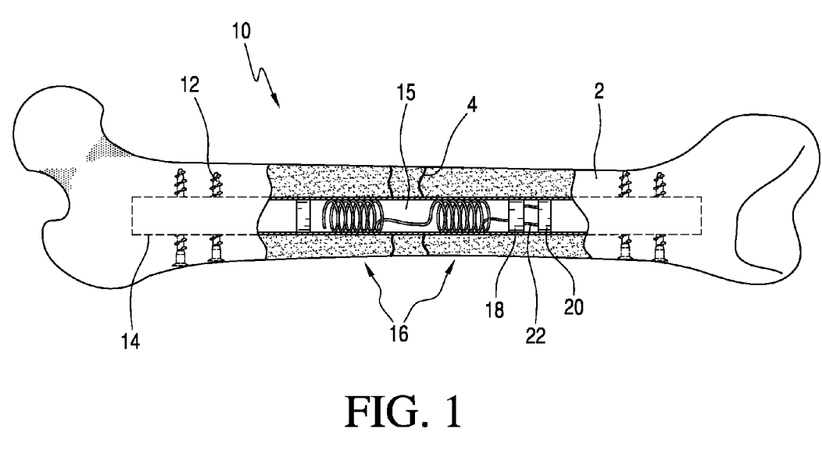
FIG. 1 is a diagram of a fixation device according to a first embodiment of the disclosure.

FIG. 1 shows a fixation device 10 according to a first embodiment of the invention. The fixation device generally includes a hollow rod 14 which is an intramedullary fixation device. Such intramedullary fixation devices are conventionally known for placement within a bone cavity, especially longer bones such as the femur or the tibia to aid in proper realignment of a bone 2 having a fracture 4. Like conventional intramedullary rods, the hollow rod 14 illustrated in FIG. 1 may be held in place using screws 12 such as locking screws. Preferably the rod is fabricated in a size and shape that give it sufficient strength to stabilize the fracture during healing. The rod is fabricated from a material that permits a magnetic field to pass there through, either because the material itself permits the passage of a magnetic field or the rod is provided with a section through which the magnetic field may pass.

Unlike conventional intramedullary rods, a fixation device 10 according to the illustrated embodiment includes an electromagnetic field emitter 16 disposed in the cavity 15 of the hollow rod 14. The electromagnetic field emitter 16 may take any conventional shape, and preferably includes an electromagnetic coil such as a solenoid coil through which a current is passed to create a magnetic field.

A controller 18 which may be fabricated on a printed circuit board and/or as an integrated circuit is provided in communication with the electromagnetic coil of the electromagnetic field emitter 16 for generating a signal to energize the electromagnetic field emitter 16. In the embodiment of FIG. 1, a power source 20, such as a battery, also is provided within the hollow rod, in communication with the electromagnetic field emitter 16 and the controller 18. Leads or wires 22 also are provided in the hollow rod 14 to interconnect the electromagnetic field emitter 16, the controller 18, and the power source 20. Generally speaking, the controller is energized by the power source to generate the signal that when applied to the electromagnetic field emitter creates a field, preferably a varying field that intersects the fracture or wound.

In one example of the invention, the controller 18 is programmed with a series of instructions for controlling the field emitted by the electromagnetic field emitter 16. More specifically, the controller may be programmed with a routine such as a series of intensity and/or time dependent instructions. Depending upon the program routine, the controller will manipulate the power from the power source to supply a current to the electromagnetic field emitter 16, which in turn will create an electromagnetic field corresponding to the applied current. By varying the current and the time, any number of routines may be used, as required by the patient.

The controller may be preprogrammed with a number of routines for application of varied electromagnetic fields to the injury site. For example, routines may be included that depend upon the location and/or severity of a fracture or accompanying wounds to nearby tissue and/or muscle. In still other embodiments, the controller may be programmable either before implantation into the patient, or after being inserted. One lead may be accessible through the skin to allow tethering to a computer or the like useable in programming the controller 18. Preferably, the controller will include a wireless receiver configured to receive programming instructions wirelessly from a computer or the like equipped with a transmitter. Further, the controller may include a wireless transmitter for transmitting data corresponding to the signal generated by the controller.

Although in the illustrated embodiment of FIG. 1, the power source and controller are disposed within the hollow rod with the electromagnetic field emitter, in other embodiments the power source and/or the controller may be disposed in the body, but remote from the electromagnetic field emitter. In such an arrangement, the wires or leads 22 may extend outside of the hollow rod 14 and connect to the remotely disposed controller 18 and/or power supply 20. In still other embodiments, the controller and/or the power source may be disposed completely outside of the body. For example, the power source may be a field emitter disposed outside the body that emits an electromagnetic field and when placed in proximity to an induction coil disposed in the body, will charge the coil to power the electromagnetic field generator. Preferably, the field emitter used as the power supply 20 emits a field that is different from the field generated by the electromagnetic field emitter, and which will not adversely affect the wound healing sought to be accomplished by the electromagnetic emitter.

The electromagnetic field emitter generally is a conventional structure that will emit an electromagnetic field at a frequency of between about 5 and about 100 Hz, more preferably between about 5 Hz and about 30 MHz, and at 60-400 Gauss within a treatment volume. As a result of the invention, the emitter can be placed in close proximity to a fracture in a bone and/or proximate nearby afflicted muscle or other tissue. Although two emitters are illustrated in FIG. 1, more or fewer emitters may be provided. The emitter(s) preferably are at fixed positions inside the hollow rod 14. The position of the emitter 16 within the hollow rod 14 will be dictated by the position of the rod relative to the position of the fracture. When the rod 14 is placed in the bone 2, the electromagnetic field emitter 16 will closely align with the position of the fracture to expose the fracture to the electromagnetic field. In a preferred embodiment, the emitter(s) will be affixed to the inside of the hollow rod using any known fastener, such as a physical fastener like a set screw, or an implant grade adhesive.

Figure 2:
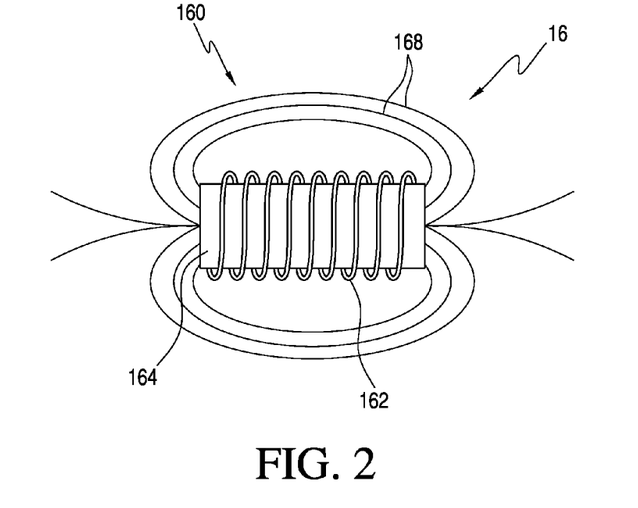
FIG. 2 is a diagram of an electromagnetic field emitter used in a fixation device according to the disclosure.

As will be appreciated by those of ordinary skill in the art, known electromagnetic field emitters produce electromagnetic fields having a known size and shape. FIG. 2 shows a conventional electromagnetic field emitter 160 including a conductive wire, such as copper, 162 wound along an axis to form a coil. When an electrical current is passed through the coil, an electromagnetic field is created as depicted by flux lines 168. Although not required, the illustrated coil 162 is wrapped around a cylindrical core 164, which is preferably a ferrous core, to intensify the field.

In use, the coil should be positioned such that the bone fracture and/or any other tissue to be healed is disposed in the electromagnetic field. An advantage of the invention over previously-used, non-implanted electromagnetic field emitters, is that the field can be generated very near to the fracture or other wound to be treated so that the high flux portion of the field can intersect the wound/fracture. This close positioning allows for a lower power requirement, because the field need not be as strong as it would need to be if it were generated farther from the fracture and increased biological healing response because the field is not interfered with by passing through surrounding tissue. When the fixation device is a rod, as in FIG. 1, a series of electromagnetic field emitters like those illustrated in FIG. 2 may be disposed along the length of the hollow rod, such that the electromagnetic fields overlap along the length of the rod. In this embodiment any position along the rod will be affected by an electromagnetic field. While the care giver could opt to energize all coils to provide a field along the full length of the rod, the controller could alternatively be configured to allow for selective energizing of the coils. In other embodiments fewer emitters may be provided that are positioned specifically for affecting the fracture/wound. One or more emitters may be provided that are moveable within the rod prior to placement of the rod, to allow the emitters to be placed at positions that will best promote healing. In yet another embodiment of the invention, the emitters may be placed at predetermined positions within different rods, with the orthopedic surgeon choosing a rod that will align the emitter with the fracture/wound for healing promotion.

In conventional intramedullary nail placement procedures, a guide wire is passed longitudinally through a fractured bone, a reamer is passed over the guide wire to bore the bone out longitudinally, and the rod is fed over the guide wire into position. Once in position, screws may be inserted transversely through the bone and into the rod, to lock the rod in place. A rod according to the present disclosure may be inserted using the same procedure. To do so, the rod preferably also has a longitudinal opening, which may require that each of the electromagnetic field emitters and other components occupy less than the full cross-sectional area of the opening in the rod or have openings extending axially therethrough.

For example, each electromagnetic field emitter could have a hole formed therethrough, large enough to allow for passage of the guide wire there through. In one embodiment, each of the emitters is a wound coil such as that shown in FIG. 2. The illustrated coil, also referred to as an air coil, is illustrated in which a wire is wound continuously along an axis preferably in multiple layers to form a cylindrical coil defining an open middle. The coil is preferably sized to allow passage of the guide wire through the open middle. In another embodiment it may be desirable to wrap the air coil around a ferrite core. To facilitate passage of the nail over a guide wire, the ferrite core may have a longitudinal opening formed therein.

Figure 3A:
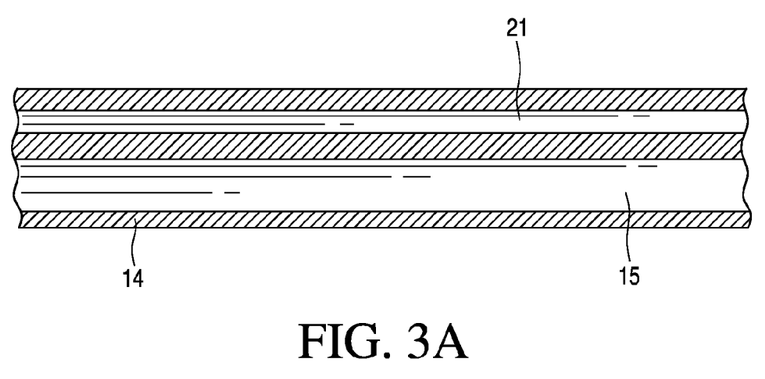
FIGS. 3A-3C are cross-sectional views of other embodiments of fixation devices according to the disclosure.
Figure 3B:
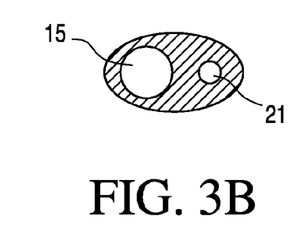
Figure 3C:
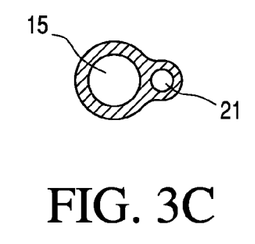

Other embodiments may also allow use of a guide wire to insert an intramedullary rod by ensuring that the footprint of the electromagnetic field emitter has a smaller area than the area of a cross-section of the opening in the hollow rod. This could be particularly useful when it is desired to dispose a solid core in the coil. For example, the emitter could be attached to a sidewall of the opening, sized small enough such that space is provided next to the emitter large enough to pass a guide wire. A sleeve or conduit could also be provided in the rod to guide the guide wire through a more tortuous path along the length of the rod. The sleeve or conduit feeds the guide wire in any number of ways, including through the sidewall of the hollow rod. This would be particularly useful in applications in which the emitter occupies substantially all of the opening in the hollow rod at axial positions along the rod. In a further example, the hollow rod may include a completely separate, substantially axial, guide opening 21, which is parallel to the cavity 15. An example of this separate opening is illustrated in FIG. 3A, and is formed in a sidewall of the hollow rod. To this end, the hollow rod may not be cylindrical, but could instead include a profile allowing for both the cavity 15 and the guide opening 21. Some exemplary profiles are illustrated in FIGS. 3B and 3C.

As will be appreciated, large, concentrated forces are often applied to intramedullary nails and rods during insertion and during healing, and the components disposed within the rod must be firmly affixed in the rod to avoid damage or dislodgement during insertion and healing.

In another embodiment of the disclosure, the electromagnetic field emitter (and power source and controller) may be inserted into the rod after the rod is inserted into the bone. A stop, such as a constriction or protuberance, may be provided in the cavity 15 of the hollow rod in such an embodiment, to attain proper axial positioning of the inserted components. An adhesive may be applied to the inserted components to maintain their position once inserted. Alternatively, a packing or mechanical stop may be inserted after the inserted components to maintain positioning of the emitter in the rod. An advantage of the after-inserted components is that the components do not undergo the pounding and potential destruction accompanying insertion of the rod.

In other embodiments, a guide wire is not used for insertion of the hollow rod, so no provisions for an axial passageway through the rod need be made. In this example, the opening through the bone is bored or reamed out using known techniques, and the rod is then inserted.

Because the fixation device 10 is generally intended to be left in the patient permanently, each of the components should be implant grade. Moreover, the hollow rod 14 of the embodiment of FIG. 1 preferably is a non-ferrous material, such as a polymer or titanium so as not to affect the electromagnetic field emitted by the electromagnetic field emitter 16. The components should be chosen such that the electromagnetic field emitted by the electromagnetic field emitter 16 will pass freely through the fixation device 10 to the fractured bone and/or the damaged tissue.

The invention is not limited to an embodiment in which the electromagnetic field emitter is disposed within a hollow rod comprising a fixation device. In an alternative to the foregoing embodiments, the electromagnetic field emitter could be disposed on a side of the hollow rod 14 or at an end thereof. In such an embodiment, it may not be necessary that the hollow rod 14 be hollow at all. A solid rod could be used instead, because no components are intended to be disposed within the rod.

Figure 4:
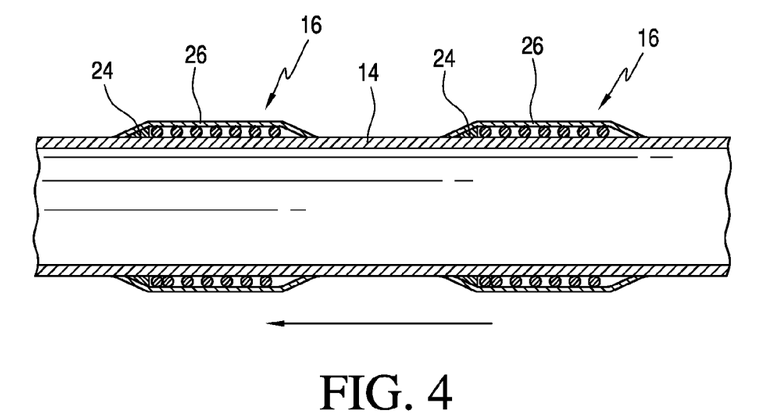
FIG. 4 is a cross-sectional view of another embodiment of a fixation device according to the disclosure.

In another embodiment, the coil comprising the emitter could be wrapped around the rod. This embodiment is shown in FIG. 4. In that figure, emitters 16 are formed at spaced positions along the rod 14 by wrapping wire around the rod 14. Although this embodiment shows a plurality of discrete coils along the length of the rod, the wire may be wrapped continuously along the entire length of the rod, to create a larger field. In these embodiments, all or a portion of the rod may be ferrous, to intensify the field at each coil. Alternatively, the rod could still be hollow, but with ferrous material disposed in the hollow rod. The control and power supply could also be disposed in a hollow rod.

The embodiment illustrated in FIG. 4 also includes a protective layer 26 formed over the coils. This protective layer 26 preferably is chosen to shield the coils from damage when the rod is inserted by an orthopedic surgeon. For example, the protective layer may be a polymeric or foil wrap disposed over the coil, and which will not affect the field emitted by the coils. FIG. 4 also shows a leading protrusion 24 disposed axially adjacent to each coil. The protrusion extends radially from the rod further than the coil and is disposed such that when the rod is inserted along the direction of arrow in FIG. 4, the protrusion first enters the bone. In this manner, the protrusion forges a path through the bone to minimize contact of the bone with the coil, thereby reducing the potential for damage to the coil.

In alternatives to FIG. 4, one or both of the protective layer 26 and the protrusion 24 may not be provided. The protrusion may be an annular ring disposed about the circumference of the rod, or it may be a series of protrusions disposed about the circumference. Moreover, as illustrated in FIG. 4, the protrusion preferably is angled, to promote ease of insertion of the rod into the bone.

Figure 5:
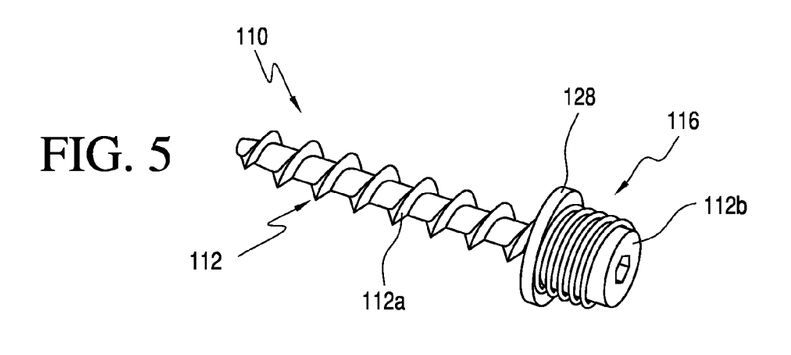
FIG. 5 is a perspective view of a fixation device according to another embodiment of the disclosure.

The invention also is not limited to an intramedullary rod or nail. FIG. 5 shows an embodiment of the invention in which a fixation device 110 is incorporated in a screw 112 having a threaded shaft 112a and a head 112b. There, an electromagnetic field emitter 116 comprising a plurality of windings as a coil like that in FIG. 2 is disposed on a shaft of the screw 112, proximate the head 112b. The electromagnetic field emitter thus will not inhibit access to the head of the screw, for example, for insertion, but the emitter can be placed wherever a screw can be inserted. The screw may be a locking screw such as the type used in connection with an intramedullary rod or a plate, or it may be any other type of screw, including but not limited to a pedicle screw for use in spinal procedures.

As also illustrated in FIG. 5, the screw 112 further includes an annular stop 128 arranged between the threads and the coil. When an orthopedic surgeon inserts the screw, rotation of the screw will be stopped when the stop 128 contacts the bone or plate into which the screw is being inserted. In this way, the surgeon will not overtighten the screw in a manner that will cause the coil to contact the bone or plate, resulting in potential damage to the coil. Although not illustrated, leads will extend from the coil to the controller and/or power source, as in previous embodiments. Such components may be provided on the screw, or in a separate implant.

Figure 6:
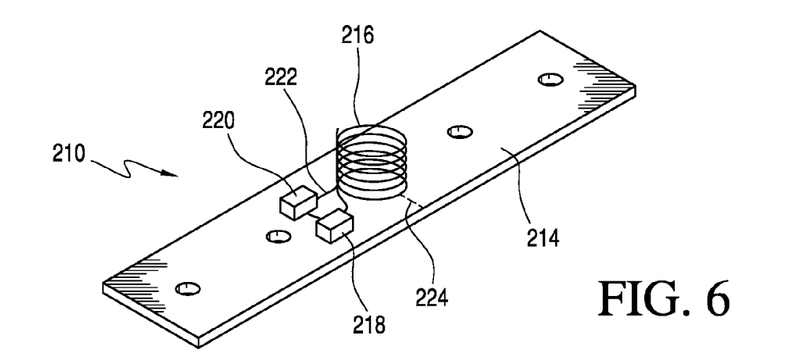
FIG. 6 is a perspective view of a fixation device according to another embodiment of the disclosure.

Yet another embodiment of the invention is illustrated in FIG. 6. FIG. 6 is similar to the previous embodiments in that it shows a fixation device 210 including an implant 214 and an electromagnetic field emitter 216. Unlike the other embodiments, the implant is a plate 214, such as a surgical or orthopedic plate, and the emitter 216 is a coil carried on the plate. The plate may be any known plate or plate-like structure, for example, such as used to maintain position of a fractured bone for healing that bone or for fusion of bones, as in spinal surgery. In the preferred embodiment, the emitter 216 is carried on a side of the plate 214 that does not contact the bone. The emitter 216 may be fixed to the plate in any number of ways, including fasteners and adhesives. FIG. 6 also shows a controller 218 and power source 220 carried on the plate, and electrical leads 222 interconnecting the foregoing components. It is preferred that the plate be made from a material that will not distort the field generated by the emitter, but the emitter and plate may be designed to cooperate in creating a field that will effectively intersect with a fracture/wound.

The emitter may be mounted on any position of the plate, to ensure maximum exposure of the fracture to the generated field. In some embodiments, the orthopedic surgeon will affix the emitter during surgery, using known fastening means, such as adhesives or mechanical fasteners. In other embodiments, an emitter or emitters may be fixed at predetermined position(s) on the plate. The surgeon will then choose the appropriate plate, and place the plate to ensure that the emitted field is properly aligned with the injury. FIG. 6 also illustrates indicia or a registration mark 224 (a dotted line in the figure) that will allow a user to readily properly align the plate for healing using the emitter. In the illustrated embodiment, the surgeon aligns the dotted line 224 with the break to ensure that the emitter will be properly aligned.

Figure 7:
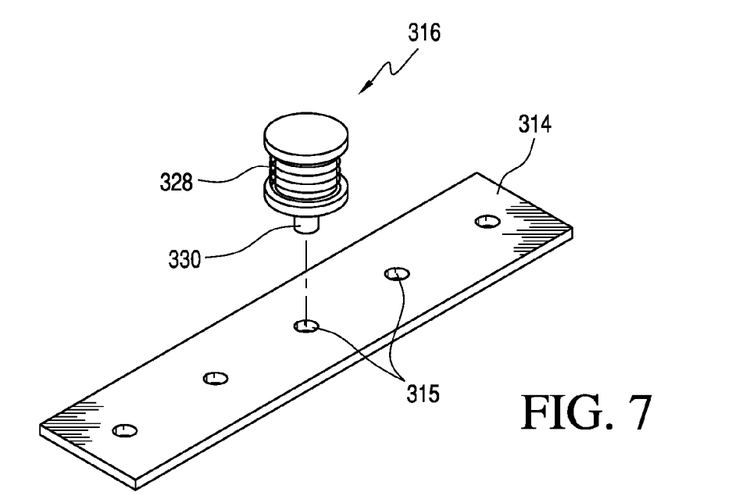
FIG. 7 is a perspective view of a fixation device according to another embodiment of the disclosure.

In yet another embodiment, illustrated in FIG. 7, an emitter 316 includes a coil 328 such as those described above and a protrusion 330 depending from the coil. The protrusion 330 is sized to allow for registration of the emitter 316 with any standard hole 315 formed in an orthopedic plate 314. As will be appreciated, orthopedic plates generally have a plurality of holes 315, to allow a surgeon maximum flexibility for affixation of the plate to the bone. Any hole or holes aligning with the fracture are generally not used, because a screw is rarely used at the break. However, it is beneficial to align the emitter with the break, for reasons discussed above. The protrusion 330 of this embodiment allows for registration of the emitter with the plate at the break. The protrusion may form a press or interference fit with the plate, facilitating connection of the emitter with the plate. Alternatively, the emitter with protrusion may be fixed to the plate using any known fastening method, such as adhesives. A controller and/or a power source may be included with the emitter or may be positioned anywhere on or spaced from the plate.

Although the foregoing embodiments describe securing the emitter to the top of the plate, the emitter may be disposed anywhere on the plate, including on an edge of the plate or the bottom of the plate, proximate the bone to which the plate is affixed. In another embodiment, illustrated in FIG. 8, an electromagnetic field emitter 316 is disposed in a recess 313 formed in a plate 314. The plate 314 further includes holes 315 for affixation of the plate. A controller 318 and a power source 320 are also illustrated in the recess 313. The recess 313 allows for a lower-profile arrangement than can be achieved by placing the emitter on top of the plate. The recessed portion of the plate should be configured to provide sufficient rigidity to stabilize the fracture and minimize the formation of stress risers.

Figure 8:
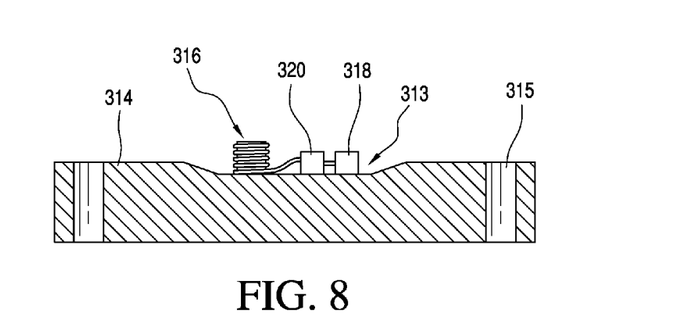
FIG. 8 is a cross-sectional view of a fixation device according to another embodiment of the disclosure.
Figure 9:
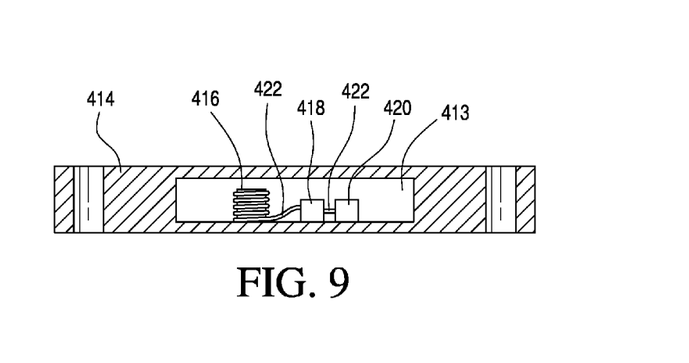
FIG. 9 is a cross-sectional view of a fixation device according to another embodiment of the disclosure.

FIG. 9 is a modification of the embodiment of FIG. 8 in which an emitter 416, a controller 418 and a power supply 420, with interconnections 422, are completely encapsulated within an orthopedic plate 414. In this embodiment, a cavity 413 is provided in the plate 414 and the components are disposed in the cavity. To facilitate formation of the plate 414, the plate may be made of multiple pieces that are assembled after affixation of the emitter 416 and other components to one of the pieces. For example, the plate may have first and second opposing pieces, e.g., a top and a bottom having facing horizontal surfaces that when assembled define a cavity sized to receive the emitter and other components, as appropriate. Alternatively, the plate may be formed with a recess, as in FIG. 8, the components placed in the recess, and then a cover applied to substantially encapsulate the components in the plate. In such embodiments, the surgeon will preferably receive a unitary piece in which is embedded the components, such as the emitter, controller and power supply.

As with previous embodiments, the plate used in FIGS. 6-9 preferably is non-ferrous, such that the emitted electromagnetic field will readily pass through the plate to the treatment area.

Figure 10:
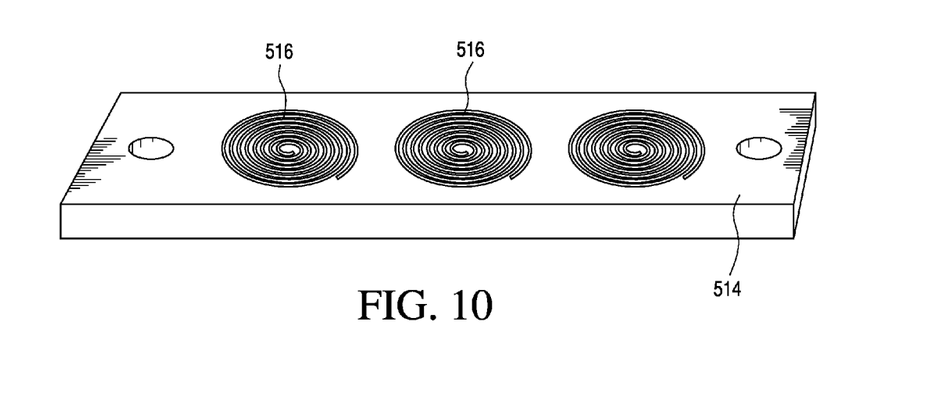
FIG. 10 is a perspective view of a fixation device according to another embodiment of the invention.
Figure 11:
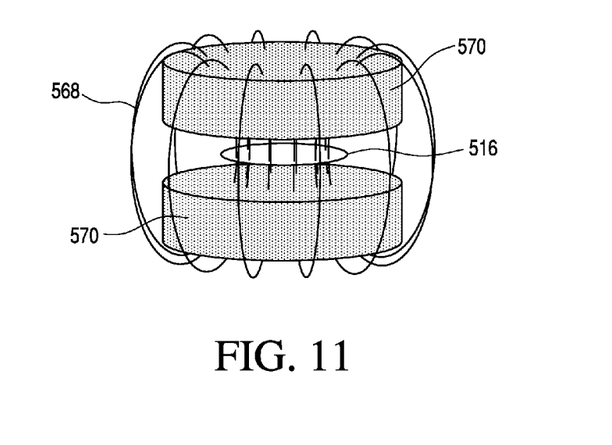
FIG. 11 is a perspective view of a field generator and an associated generated field.

Although the embodiments illustrated until now utilize air or axial coils such as those illustrated in FIG. 2, other types of coils may be used. FIG. 10 shows an embodiment in which the electromagnetic field emitter is a flat or pancake coil 516 disposed on a plate 514, such as an orthopedic plate. A pancake coil generally emits a field having flux lines 568 such as those illustrated in FIG. 11. FIG. 11 also illustrates treatment regions 570, which are areas disposed in the magnetic field. In practice, the afflicted bone or tissue to be healed should be disposed in these treatment regions 570 for maximum efficacy of the emitter 516.

In the embodiment of FIG. 10, a plurality of pancake coils is provided in a two-dimensional array, i.e., a 1×4 matrix, on a plate 514. Using appropriate controls, the coils may be selectively energized at desired frequencies and for preferred durations. For example, when a plate such as that illustrated in FIG. 10 is used, the coil or coils closest to the fracture site will be energized according to a first treatment methodology. Other coils may be energized differently or not at all. In other embodiments, more or fewer pancake coils may be provided. Moreover, the pancake coils may be encapsulated in the plate, instead of disposed on the plate, as in the embodiment of FIG. 9.

Figure 12:
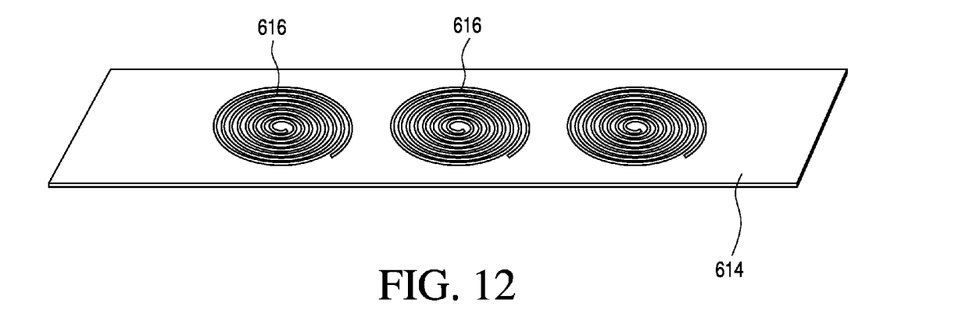
FIG. 12 is a perspective view of a series of coils on a substrate, according to another embodiment of the invention.

Another embodiment of the invention is illustrated in FIG. 12. There, a plurality of pancake coils 616 is provided on a flexible substrate 614. The flexible substrate allows for form-fitting of the array of coils to a surface. The array of coils may be formed from wrapped wire, but more likely will be formed by depositing a metal, such as copper, onto the substrate as a coil using known deposition, including known masking and/or etching, techniques. The deposited coil may be a single-layer coil or may include turns in multiple layers. That is, deposited pancake coils may be stacked one on top of the next. In such a configuration, an intermediate layer, such as an insulating layer, may also be provided between stacked coils. Such an arrangement will provide an increased number of turns for the coil, but still provide a relatively low profile.

The substrate according to the embodiment of FIG. 12 preferably is made of a polymer-blend. The flexible substrate may be affixed to a plate, such as a conventional plate, or in some embodiments could be affixed directly to a patient's bone. An adhesive may be disposed between the back of the substrate and the site to be treated to adhere the substrate. The adhesive may be pre-applied and exposed by removing a backing or other protective coating, or it may be applied at the time of affixation of the substrate. The substrate could otherwise be affixed using any known methodology.

The flexible substrate with electromagnetic emitters has the benefit of allowing for adaptation of existing orthopedic devices, i.e., by affixing the substrate to such devices. Any number of fixation devices could be modified to include a substrate including coils. For example, one or more coils on a flexible substrate may be disposed on an intramedullary rod, either wrapping around the rod, or along the length of the rod. In other uses, the substrate could be applied directly to a bone or other anatomical structure in the body.

In any of the foregoing embodiments, it is preferable to arrange the electromagnetic field emitter such that in use the emitted field acts on the desired treatment area. Although the embodiments of FIGS. 6-11 generally illustrate coils with axes perpendicular to a top surface of a plate, the coils could readily be provided "on their side" such that their axis is parallel to the top surface of the plate without departing from the spirit and scope of the invention.

In several embodiments described above, a device according to the invention generally includes an implantable device, such as a conventional device like a rod or plate, adapted to carry a field emitter and a signal generator. Other combinations also are contemplated. The field emitter and signal generator also may be carried by an implant such as a prosthesis. For example, during a hip replacement, a portion of the femur is removed and replaced with an implant including a new ball attached to a stem and a cooperating piece including a socket. The field emitter and signal generator may be carried by the ball or by the shaft of the implant. In one embodiment, the ball and/or shaft may be hollow, with the field emitter and signal generator being disposed in the hollow ball or shaft. Those of ordinary skill in the art will appreciate that alternative, similar embodiments can also be achieved using the teachings of this disclosure.

The power source provided in the invention may be any known or developed power source sufficient to power the coil. Batteries have been conventionally implanted into the human body, e.g., in pace makers, and such powering technology may be applicable with embodiments of the invention.

The control circuitry preferably is provided to allow for user selection of strength and duration of currents applied to the electromagnetic emitters. The controller may be programmable, i.e., via remote control through an input device external to the patient, to allow for custom treatment of each patient. In other embodiments, the controller could be pre-programmed with a treatment methodology and merely turned on to run through that pre-determined treatment regimen. The control circuitry may further include wake-up circuitry or the like, to allow for delayed operation. For example, an orthopedist may determine that they would prefer not to use the electromagnetic field therapy until some amount of time after surgery. Thus, the emitter should not be energized until that time, if at all.

As noted above, a number of arrangements of electromagnetic field emitters, signal generating electronics, i.e., to instruct energizing of the coil, and power sources, which provide power for energizing the coil, will be appreciated from this disclosure. In a relatively simple embodiment, a battery, as the power source, the signal generating electronics, and a wire coil are implanted directly in a patient. The signal generating electronics will include pre-programmed operational sequences as treatment routines that will energize the coil as desired.

In addition to a battery, signal generating electronics and a magnetic coil, the implanted device may further include a receiver and a transmitter, allowing the device to communicate with an external device. Such an arrangement would allow for downloading to the implanted device signal patterns and schedules, e.g., for specific treatments, as well as updates, and for receiving information from the device, for example, about the treatment, such as accumulated dosimetry and/or other treatment characteristics.

In yet another embodiment of the invention, to assist in providing useful information about the device implanted into the body, the device may further include sensory coils. Such coils are spaced from the electromagnetic field emitters to receive the generated magnetic field at a known distance from the generating coil. The receiver coil is placed at a position, such as a position spaced along the implanted device away from the emitter or an opposite side of a fracture to be treated, to measure the magnitude and duration of the generated magnetic field. Using the aforementioned transmitter, the results measured by the sensor coil are then forwarded to the remote device, for interpretation by a doctor or technician.

Although many of the foregoing embodiments entail implanting a battery as a power source, in some applications a battery may not be the best power source. For example, it may be impractical to use a conventional battery, for example, because the battery may not last long enough. When chronic pain is being treated using a device according to the invention, it is preferable that the device function as long as the patient requires. Thus, the device may further include an induction coil as a rechargeable power source. More specifically, the induction coil is implanted in the patient and an induction device, such as an induction wand, is used external to the patient to charge the device. The wand may take any known form including being provided in a wearable device that could charge the device, for example, when the user is sleeping.

Figure 13:
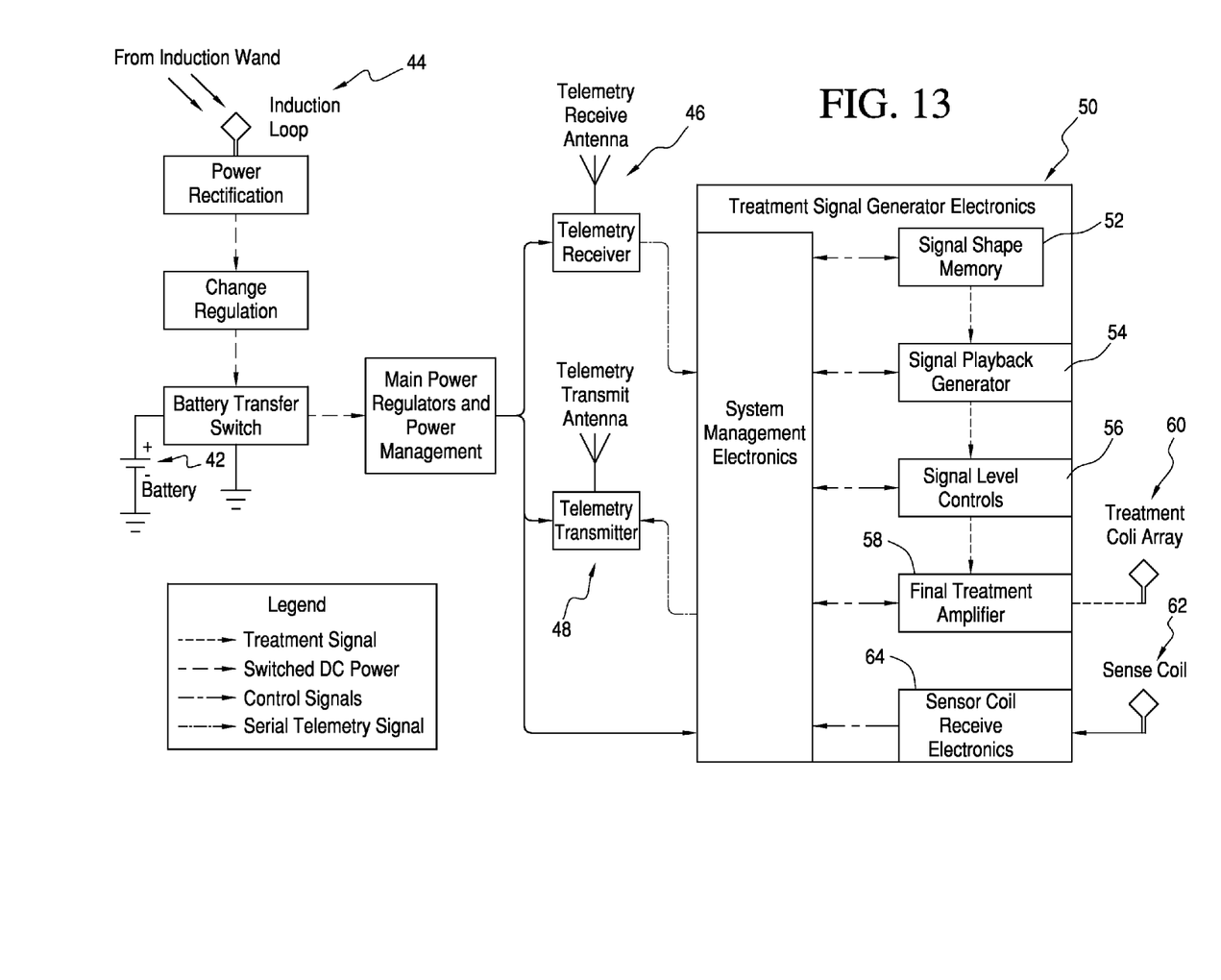
FIG. 13 is a schematic illustrating a system according to another embodiment of the invention.

FIG. 13 illustrates a schematic of a system according to the invention. There, a battery 42 is the power source, and an induction loop 44 is provided to charge the battery 42. A receiver 46 and transmitter 48 are also illustrated, as is an example of the signal generator 50. The signal generator 50 is illustrated as including a signal shape memory 52, which stores one or more signal shapes used to drive the coil 60; a signal playback generator 54; signal level controls 56; and final treatment amplifier 58. These components all are connected to the treatment coil 60. The schematic also shows a sensor coil 62, such as that described above, and controls 64 for receiving information from the sensor coil 62. This schematic is provided merely as an example; other systems and configurations will be apparent to those of ordinary skill in the art upon being educated by this disclosure.

Figure 14:
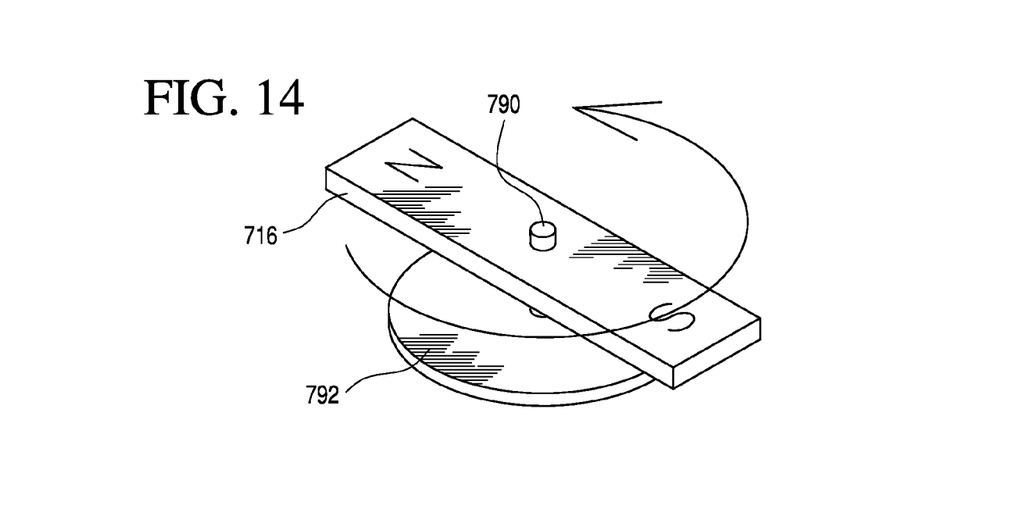
FIG. 14 is a perspective view of a fixation device according to another embodiment of the invention.

The invention has been generally described herein as utilizing a coil as an electromagnetic field emitter. Other embodiments may include different field generators. For example, an alternative embodiment may include a permanent magnet, having a known field strength and shape. The magnet could then be vibrated, rotated or otherwise moved to modulate the field, to apply the desired bioeffect. FIG. 14 shows an example of this. There, a permanent magnet 716 generates a magnetic field having a known strength and shape. The magnet 716 is disposed on a shaft 790, rotatable by a rotary actuator 792, such as a piezoelectric actuator. By rotating the magnet, the magnet's field is modulated, which modulation may be optimized for treatment of a broken bone or wound. Thus, the actuator/permanent magnet combination forms a controllable magnetic field emitter. Although not illustrated, the actuator/permanent magnet field emitter will be carried on a fixation device or other implantable carrier, such as an orthopedic plate, intramedullary rod, replacement implant, or the like.

Figure 15:
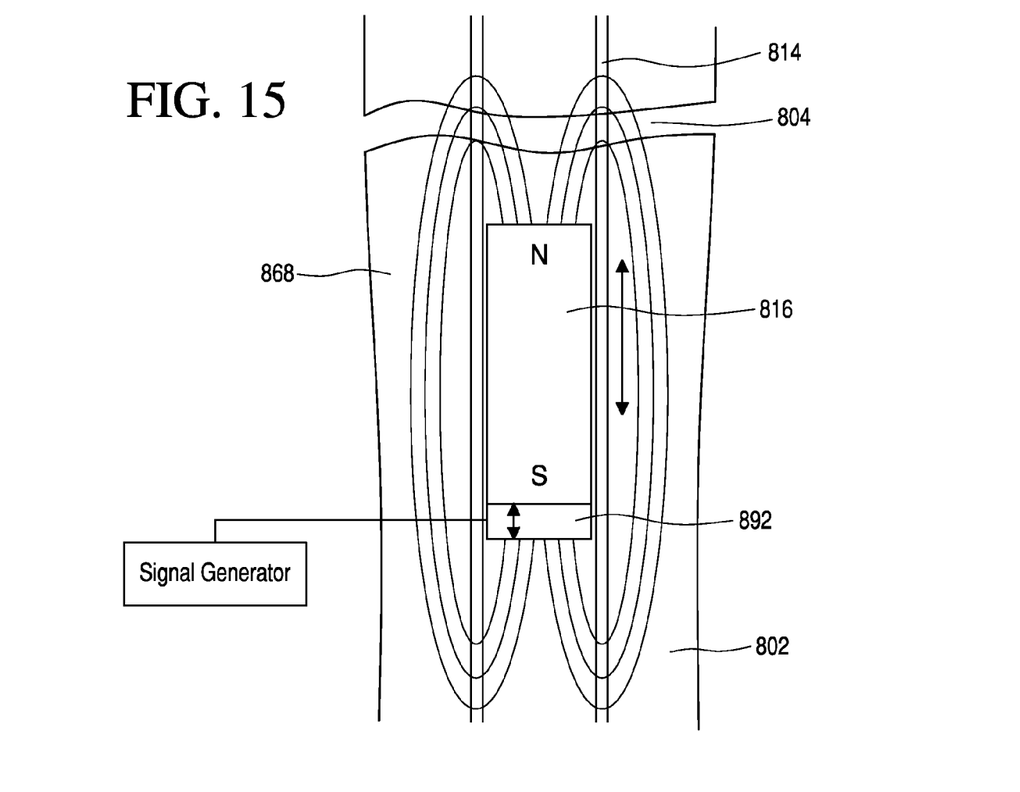
FIG. 15 is a plan view of a fixation device according to another embodiment of the invention.

Although a rotary actuator is illustrated in FIG. 14, this is merely for illustrative and exemplary purposes. In an alternative embodiment, shown in FIG. 15, the magnet 816 is provided on a linear actuator 892, such as a piezoelectric actuator, disposed to move along the direction indicated by the arrow in FIG. 15. By actuating the actuator 892, a fracture 804 in a bone 802 is selectively disposed in and spaced from the magnet's field, indicated by flux lines 868. A signal generator for driving the actuator also is shown in FIG. 15. The magnet 816 and the actuator 892 are illustrated in this embodiment as being disposed in a hollow rod 814. In other embodiments those components could be carried on any other implant, including but not limited to those described above While the invention has been described in connection with several presently preferred embodiments thereof, those skilled in the art will appreciate that many modifications and changes may be made therein without departing from the true spirit and scope of the invention which accordingly is intended to be defined solely by the appended claims.

The invention claimed is:

1. An orthopedic device comprising:
an internal orthopedic fixation device;
a plurality of electromagnetic field emitters carried by and affixed to or contained within the fixation device;
a power source for powering the plurality of electromagnetic field emitters;
a controller for controlling an electromagnetic field emitted by the plurality of electromagnetic field emitters; and
wherein the fixation device is a plate or an intramedullary rod, and the plurality of electromagnetic field emitters are disposed along the length of the fixation device, all of the electromagnetic field emitters configured to project electromagnetic fields, the electromagnetic fields oriented in parallel and configured to treat a tissue fracture.

2. The orthopedic device of claim 1, wherein the power source is a battery configured to be implanted in the human body with the fixation device and the one or more electromagnetic field emitters.

3. The orthopedic device of claim 1, wherein the power source is a field generator generating a field that will charge the plurality of electromagnetic field emitters.

4. The orthopedic device of claim 3, wherein the field generated by the field generator is different from the electromagnetic field emitted by the plurality of electromagnetic field emitters.

5. The orthopedic device of claim 1, wherein the fixation device comprises a hollow intramedullary rod and the plurality of electromagnetic field emitters is disposed in the hollow intramedullary rod.

6. The orthopedic device of claim 1, wherein the fixation device is a plate.

7. The orthopedic device of claim 6, wherein the plate comprises a cutout adapted to receive the one or more electromagnetic field emitters therein.

8. The orthopedic device of claim 6, wherein at least one of the one or more electromagnetic field emitters is affixed to the plate.

9. The orthopedic device of claim 1, wherein the fixation device is an intramedullary rod, and further comprising a guidewire opening extending through the intramedullary rod.

10. The orthopedic device of claim 1, wherein at least one of the plurality of electromagnetic field emitters comprises an electromagnetic coil.

11. The orthopedic device of claim 1, wherein the electromagnetic fields are configured to treat a tissue fracture.

12. The orthopedic device of claim 1, further comprising at least one permanent magnet configured to rotate.

13. The orthopedic device of claim 1, wherein the plurality of electromagnetic field emitters are configured to emit electromagnetic fields oriented along a longitudinal axis of the fixation device.

14. The orthopedic device of claim 1, wherein the plurality of electromagnetic field emitters are configured to continuously generate electromagnetic fields for a therapeutic duration.

15. The orthopedic device of claim 1, wherein the electromagnetic fields are emitted at approximately 30 MHz.

16. A method of treating an injury comprising:
placing an orthopedic fixation device in a patient;
placing a plurality of electromagnetic field emitters carried by the device into the patient;
positioning the plurality of electromagnetic field emitters proximate to the injury;
activating at least one of the plurality of electromagnetic field emitters to emit an electromagnetic field proximate the injury; and
wherein the fixation device is a plate or an intramedullary rod, and the plurality of electromagnetic field emitters carried by the fixation device are affixed to or contained within the fixation device and comprise a plurality of electromagnetic field emitters disposed along the length of the fixation device, all of the electromagnetic field emitters configured to project electromagnetic fields, the electromagnetic fields oriented in parallel and configured to treat a tissue fracture.

17. The method of claim 16, wherein the step of activating one of the electromagnetic field emitter comprises controlling the emitter to deliver a prescribed electromagnetic field regimen.

18. The method of claim 17, wherein the regimen includes one or more of predetermined frequencies and durations.

19. The method of claim 16, further comprising securing the fixation device to a bone of the patient.

20. The method of claim 16, further comprising powering the electromagnetic field emitter with a power supply.

21. The method of claim 20, wherein the power supply is placed in the patient alone with the fixation device.

22. A device for stabilizing a fracture and promoting healing, comprising:
an intramedullary orthopedic fixation device having at least one opening therein;
a plurality of electromagnetic field emitters disposed in or affixed on the intramedullary orthopedic fixation device;
a controller communicating with the plurality of electromagnetic field emitters to control an electromagnetic field emitted by the plurality of electromagnetic field emitters;
a power source providing power to the controller and the plurality of electromagnetic field emitters, all of the electromagnetic field emitters configured to project electromagnetic fields, the electromagnetic fields oriented in parallel and configured to treat a tissue fracture; and wherein the at least one opening in the intramedullary orthopedic fixation device comprises a guidewire opening extending through the intramedullary orthopedic fixation device.

23. The device of claim 22, wherein the plurality of electromagnetic field emitters comprise a plurality of electromagnetic field emitters that are movable within the orthopedic fixation device or comprise a series of electromagnetic field emitters disposed along the length of the orthopedic fixation device.

24. The device of claim 22, wherein at least one of the plurality of electromagnetic field emitters and the controller are disposed in an opening of the intramedullary orthopedic fixation device.

25. A method of treating tissue, comprising:

applying the device of claim 1 to a bone comprising a fracture;

positioning the device such that the electromagnetic field emitters are positioned in proximity to the bone fracture; and, treating the bone fracture with the electromagnetic fields for a therapeutic duration.

\* \* \* \* \*

UNITED STATES PATENT AND TRADEMARK OFFICE
CERTIFICATE OF CORRECTION

PATENT NO. : 10,004,916 B2
APPLICATION NO. : 14/547513
DATED : June 26, 2018
INVENTOR(S) : Rogachefsky et al.

Page 1 of 1

It is certified that error appears in the above-identified patent and that said Letters Patent is hereby corrected as shown below:

In the Specification

In Column 1, Line 7 (Approx.), change "of" to --of,--

In Column 11, Line 23 (Approx.), change "above" to --above.--

In the Claims

In Column 12, Line 54, Claim 21, change "alone" to --along--

Signed and Sealed this
Thirtieth Day of October, 2018

Andrei Iancu
*Director of the United States Patent and Trademark Office*